United States Patent [19]

Kaneko et al.

[11] 4,297,441

[45] Oct. 27, 1981

[54] PHOTOGRAPHIC MATERIAL

[75] Inventors: Yutaka Kaneko; Satoshi Kawakatsu; Shigeto Hirabayashi; Hidetaka Ninomiya, all of Hino, Japan

[73] Assignee: Konishiroku Photo Industry Co., Ltd., Tokyo, Japan

[21] Appl. No.: 163,347

[22] Filed: Jun. 26, 1980

[30] Foreign Application Priority Data

Jun. 28, 1979 [JP] Japan ............................. 54/82175

[51] Int. Cl.$^3$ ............................................. G03C 1/06
[52] U.S. Cl. ................................... 430/543; 430/551; 430/566; 430/599; 430/607; 430/608; 430/612; 430/613

[58] Field of Search ............... 430/550, 551, 599, 600, 430/607, 608, 612, 613, 543, 407, 411, 264, 566

[56] References Cited

U.S. PATENT DOCUMENTS

| | | | |
|---|---|---|---|
| 3,445,235 | 5/1969 | Burt | 430/608 |
| 3,725,078 | 4/1973 | Bigelow | 430/607 |
| 3,761,275 | 9/1973 | Bigelow | 430/599 |
| 3,785,823 | 1/1974 | Bigelow | 430/266 |

*Primary Examiner*—Mary F. Downey
*Attorney, Agent, or Firm*—Bierman & Bierman

[57] ABSTRACT

This invention relates to photographic materials containing an ion pair compound which has a quaternary nitrogen atom as a cation and a boron compound as an anion.

8 Claims, No Drawings

PHOTOGRAPHIC MATERIAL

The present invention relates to photographic material, particularly to silver halide photographic material.

So far the photographic working function of silver halide photographic material has been well known, that is for example, the fact that an agent for photographic use, having such the working function as color developing, black and white developing, development restraining, development accelerating, or photographic sensitising and so on, is contained firstly in a processed composite or silver halide photographic material which is to be applied for development to form a photographic image, and it is more preferable to contain the said reagent in photographic material, because it is not so necessary to add many components in processing composite that the processing is more simplified. And there are certain agents for photographic use which are not stable in existence of alkali and unable to keep storage life of processing solution, and which react with other agents of photographic use during the storage period of processing solution, and which do not dissolve in processing solution at the necessary degree of concentration therefore, it is preferable that some of agents for photographic use are added in photographic material.

Further in another example, an agent should be applied at a certain specific time during a course of developing process, and is required to be contained in a specific layer of photographic material.

In the above examples, an agent is stable and immobile or non-diffusible and preferably is contained into a desired layer of a specific photographic material so as to enable to utilize it if necessary during a course of developing process.

Particularly among those agents for photographic use, nitrogen atom containing organic bases are of important and a remarkable numbers of their chemical compounds are in practical use.

For example, aromatic primary amine compounds are being practically used as color developing agents, p-aminophenol compounds as black and white developing agents, hydrazine compounds as fogging agents for direct positive type photographic sensitized materials, nitrogen atom containing hetero cyclic compounds as stabilizing agents, inhibiting agents, or toning agents, and hydroxylamine compounds as preserving agents, respectively.

Besides, it has been well known that N,N,N',N'-tetraalkyl-p-phenylenediamines and alkylamine compounds accelerate development, and that a certain kind of amino acid (e.g. L-cysteine) has a photographic sensitizing function.

So far it has been usual way to make almost all of the said nitrogen atom containing organic bases contain into a developer or other processing solution that is utilized to form a photographic image, and an attempt to make it contain into photographic material was not done much.

The reasons for the above are pointed out that many of nitrogen atom containing organic bases are oxidized very easily in the air, and that some kinds of nitrogen atom containing organic base are reacted easily with silver halide and then diminution of photographic sensitivity and stain, etc. are caused. Another reason for the above is pointed out that many of the said nitrogen atom containing organic bases are of immobile or non-diffusible whose molecules are not large enough, therefore the said base moves or diffuses easily from a desired layer in a photographic material, in which layer the base has been firstly contained, to other undesirable layer during a period of preparing or storing photographic material.

Some of the methods to make nitrogen atom containing organic bases contain stably into photographic material have been so far well known. Particularly with aromatic primary amine developing agent, the various methods to contain stably have been attempted by reason of extremely instability of the base in comparison with other agent for photographic use.

For example, in the U.S. Pat. No. 3,342,599, Schiff's base, that is obtained by the reaction with the said amine developing agent and salicylaldehyde, is used as developing agent precursor. In the U.S. Pat. No. 3,719,492, metallic salt such as lead and cadmium, etc. is used along with the said amine developing agent. In the British Pat. No. 1,069,061, precursor of phthalimide derivative, that is obtained by reaction with aromatic primary amine and phthalic acid, is used. In the Japanese Patent Laid-Open-to-Public Publication No. 53-111729, aromatic primary amine and cyclic $\beta$-dicarbonyl compound are used along with together. In the Japanese Patent L-O-P No. 53-135628, a precursor, that is obtained by reacting with aromatic primary amine and substituted or unsubstituted ($\beta$-benzenesulfonyl)ethoxycarbonyl, is used. Moreover, in the West German Pat. Nos. 1,159,758 and 1,200,679 and the U.S. Pat. No. 3,705,035 and so forth, the various methods have been described.

However, even if any one of the technique of all the above is used, it can not satisfy all the problems, that is, enough color density, diminution of photographic sensitivity during a storage period of photographic material and occurrence of fog or stain.

In order to solve the above problems, aromatic primary amine must be stably contained into photographic material, and must further be contained into a desirable layer so as not to easily react with silver halide and a coupler and so as to be of immobile or non-diffusible, and must furthermore be so treated as to fulfil the function of aromatic primary amine itself in existence of alkali.

After many experiments repeatedly carried out, the present inventors found the fact that not only aromatic primary amine but also other nitrogen atom containing organic bases can effectively be contained in photographic material.

As a chemical compounds containing a quaternary nitrogen atom is also effective as agent for photographic use, attempts to contain the compounds into photographic material have been made. For example, in the U.S. Pat. No. 3,071,465, it is described that a tetrazolium salt is contained as an anti-fogging agent. In the U.S. Pat. No. 3,719,494, it is described that a certain kind of a quarternary salt is contained as a nuclei forming agent (a fogging agent) of a silver halide emulsion.

However, stability during the storage period of photographic material containing the said compounds becomes remarkably worse, especially in color photographic material, a sharp diminution of its photographic sensitivity and increasing of stain were caused during its storage period.

It is an object of the invention to provide a technique to incorporate a chemical compound containing ammonia or a nitrogen containing organic base or quaternary nitrogen atom in photographic material which causes remarkably less occurrence of diminution of photographic sensitivity and increasing of fog or stain during a storage period of photographic material.

Another object of the invention is to provide a photographic material containing an aromatic primary amine developing, agent, which material has a high color density, and a less diminution of photographic sensitivity and a less formation of fog or stain during a storage period of photographic material.

Chemical compounds to be used in the invention are ion pair compounds of compound having quaternary nitrogen atom as cations and boron compounds as anion, which are shown in the following formula:

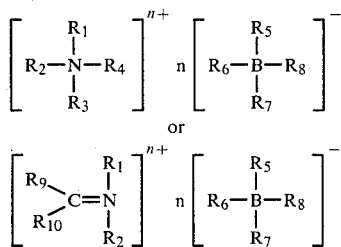

Wherein, $R_1$, $R_2$, $R_3$, $R_4$, $R_9$ and $R_{10}$ respectively represent hydrogen atom, or a hydroxyl or alkyl, alkenyl, cycloalkyl, aryl, phenyl, acyl, amino, carbamoyl, sulfonyl or 5 or 6 membered and a nitrogen oxigen or sulfur atom containing heterocyclic group. $R_1$ and $R_2$, or $R_1$ and $R_3$ may form a nitrogen containing and 5 or 6 membered hetero ring by bonding each other.

$R_5$, $R_6$, $R_7$ and $R_8$ respectively represent an alkyl, alkenyl, cycloalkyl, aryl, phenyl, heterocyclic or cyano group. They are preferably an alkyl or phenyl group individually, and more preferably all of them are same phenyl group which may be unsubstituted or substituted with a methyl group or a chlorine atom.

n represents an integral number of 1–5, and preferably n is 1. Compound of the present invention is obtained by means of a reaction of a nitrogen containing compound selected from ammonia, and a nitrogen containing organic base and a compound having a quaternary nitrogen atom, and a boron compound. As for the nitrogen containing compound, more usable is the nitrogen containing organic base, whose example is an aromatic primary amine developing agent, preferably a developing agent of type of p-phenylenediamine. Concrete example of the developing agent is shown as N-1–N-6.

Upon being heated photographic material having ammonia at elevated temperature, ammonia is discharged, and it can be obtained an advantage that alkali necessary for development may be supplied. The temperature necessary for alkali discharging is at 80°–200° C., preferably at 100°–180° C.

Nitrogen containing organic base enabling to be contained in photographic material in a manner in accordance with the invention means organic chemical compounds having basic nitrogen atom, and also chemical compounds having nitrogen atom enabling to produce a salt by reacting with hydrochloric acid, sulfuric acid or other inorganic acid. Particularly important organic base is amine compound. Either of primary amine ($R_1NH_2$), secondary amine ($R_1R_2NH$) and tertiary amine ($R_1R_2R_3N$) which hydrogen atom of ammonia is substituted with an alkyl, phenyl group or other substituting group, is a typical organic base. And there are organic bases containing nitrogen atom of amine in a ring. Pyridine, quinoline, piperidine, imidazole and derivatives thereof which may have one or more alkyl groups as substituents are the typical heterocyclic organic bases. As for other organic bases than amine, there are hydroxylamine derivatives and hydrazine derivatives, etc. Further, urea is also one of organic bases which may be used in the invention, because it can produce salt by working with hydrochloric acid. Such chemical compounds as amidine ($R_1C(NH_2)=NH$) (wherein $R_1$ is the same as defined above) also react as organic bases in the invention.

Compounds having quaternary nitrogen to be used in the invention are salts or hydroxides of quaternary covalent bonding nitrogen, that is, they mean nitrogen compounds represented by $R_1R_2R_3R_4N^+X^-$ ($R_1$, $R_2$, $R_3$ and $R_4$ may or may not be the same with each other. $X^-$ represents organic or inorganic anion or $OH^-$ ion).

The following substantial examples are given as chemical compounds containing nitrogen containing organic base and quaternary nitrogen atom which are enable to compose the said compounds used in the invention;

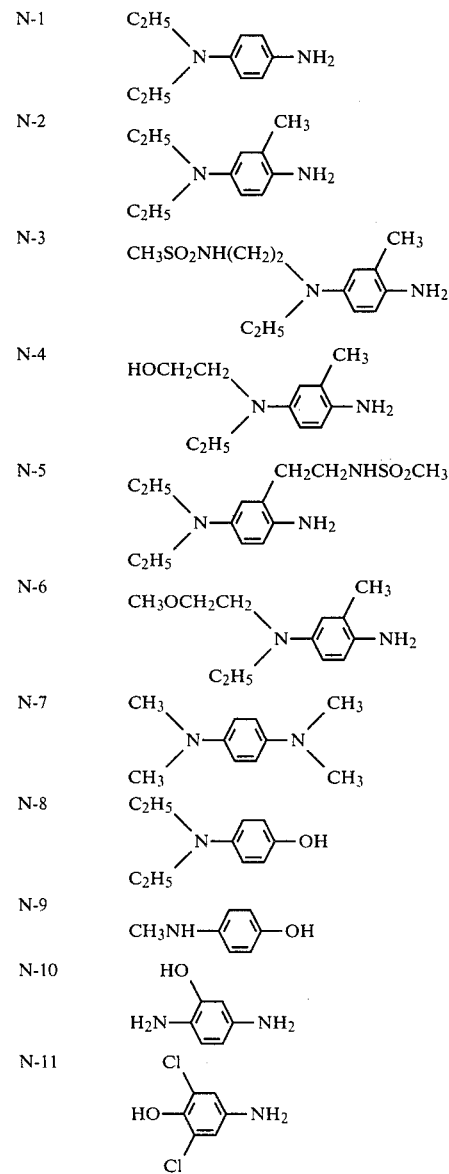

-continued

| Nos. | Chemical formulae |
|---|---|
| N-12 | HS—CH₂—CH—COOH \| NH₂ |
| N-13 | 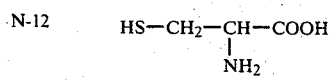 |
| N-14 | 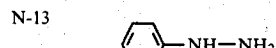 |
| N-15 | 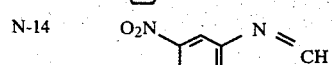 |
| N-16 | 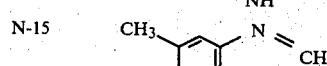 |
| N-17 | 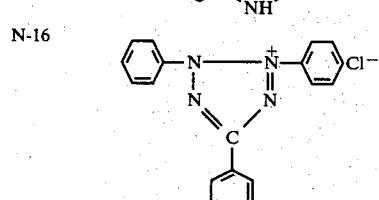 |
| N-18 | 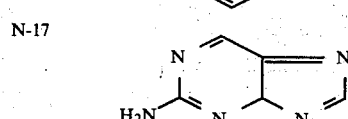 |
| N-19 | 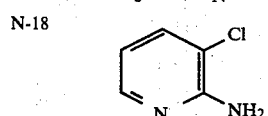 |
| N-20 | NH₂OH |
| N-21 | 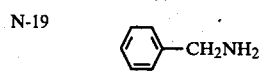 |
| N-22 | 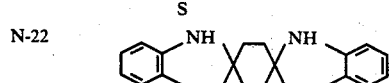 |
| N-23 | 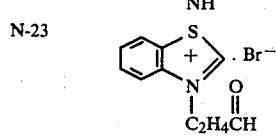 |
| N-24 | 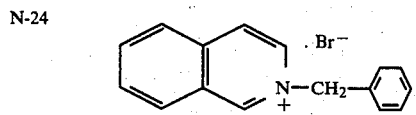 |
| N-25 | NH₃ |

The examples of the above are photographic agents which are well known generally that they may be added to display working function of color development, black and white development, development acceleration, development restraining photographic sensitising, preserving, toning and fixing and so on, into processing solution of conventional silver halide photographic sensitized material.

The substantial examples of boron compounds on the other hand, which compose the said compounds used in the invention, are shown below:

| Nos. | Chemical formulae |
|---|---|
| B-1 | 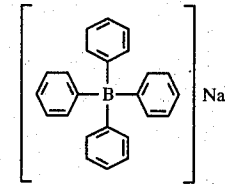 |
| B-2 | 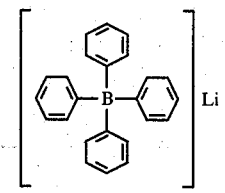 |
| B-3 | 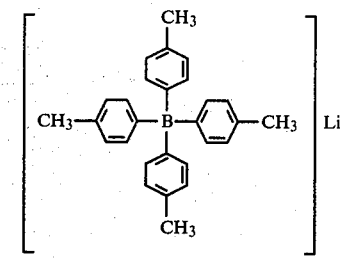 |
| B-4 | 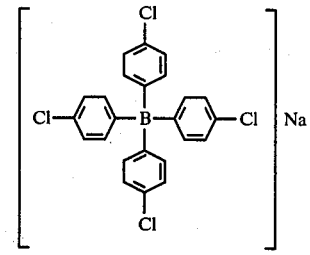 |
| B-5 | 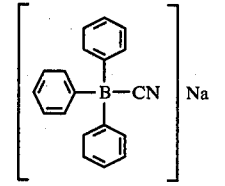 |
| B-6 | 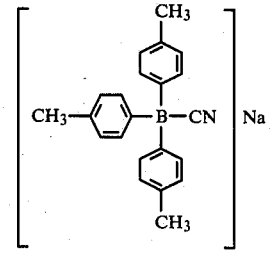 |
| B-7 | 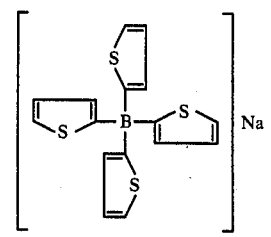 |

| Nos. | Chemical formulae |
|---|---|
| B-8 | 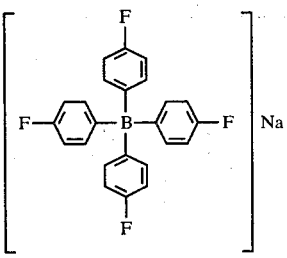 |
| B-9 | 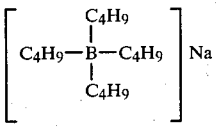 |

The above boron compounds can be composed by the methods described in the West German Pat. No. 883,147, the U.S. Pat. No. 2,853,525, Chem. Ber. 88 962 (1955), Chem. Abstr. 54 9608 (1960), 52 2667 (1958) and 52 354 (1958), Anel. Chim. Acta 32 376 (1965) and 35 1 (1966), and J. Org. Chem. 29 1971 (1964). Sodium tetraphenylborate of No. 1, inter alia, is being placed on the market as a reagent for quantitative analysis and is easy to come to hand.

The following are the substantial examples of compounds which are obtainable by reacting compounds having nitrogen containing organic base or quaternary nitrogen atom respectively with boron compound:

| Nos. | Chemical formulae |
|---|---|
| NB-1 | 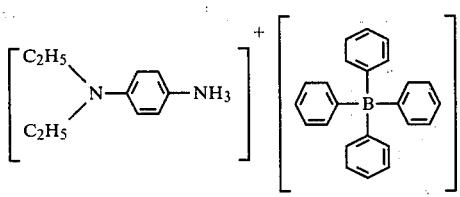 |
| NB-2 | 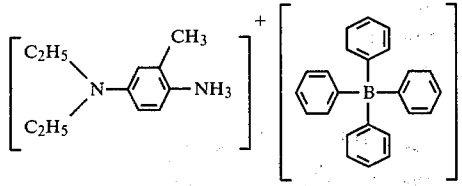 |
| NB-3 | 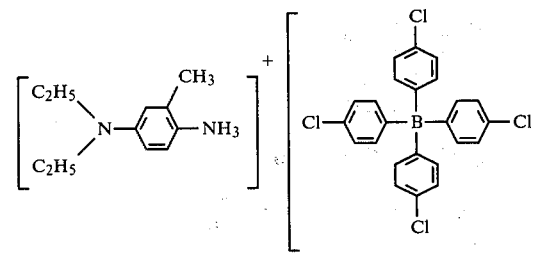 |
| NB-4 | 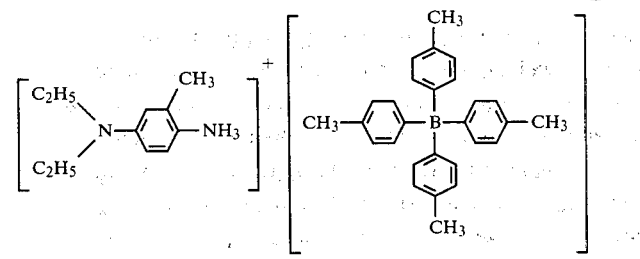 |
| NB-5 | 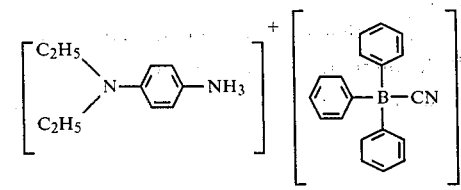 |

-continued
| Nos. | Chemical formulae |
|---|---|
| NB-6 | 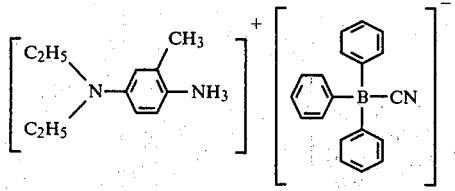 |
| NB-7 | 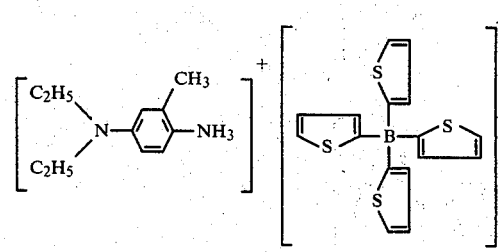 |
| NB-8 | 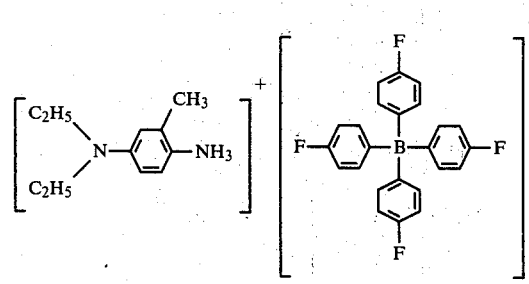 |
| NB-9 | 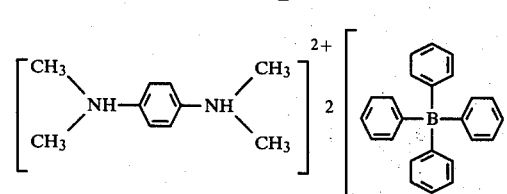 |
| NB-10 | 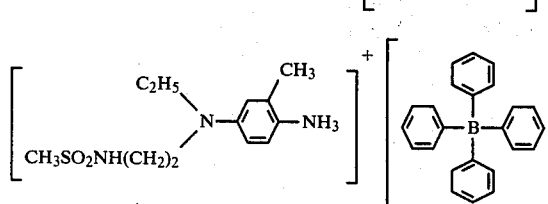 |
| NB-11 | 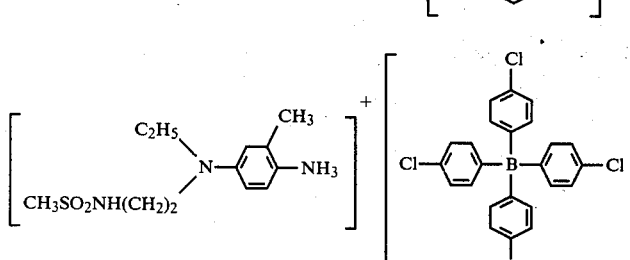 |
| NB-12 | 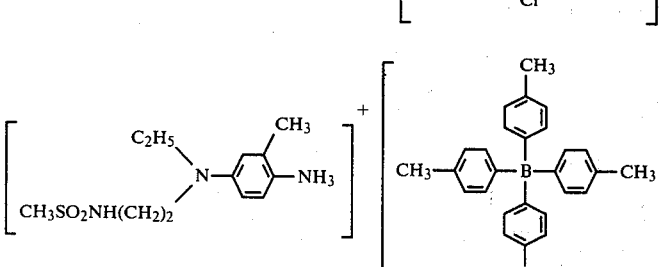 |

| Nos. | Chemical formulae |
|---|---|
| NB-13 | 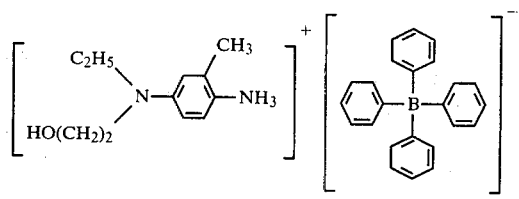 |
| NB-14 | 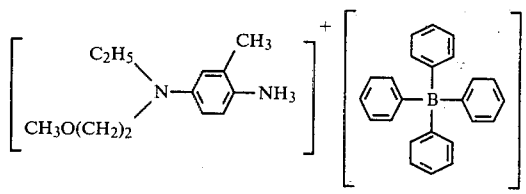 |
| NB-15 | 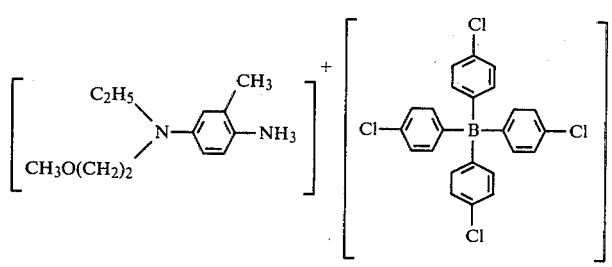 |
| NB-16 | 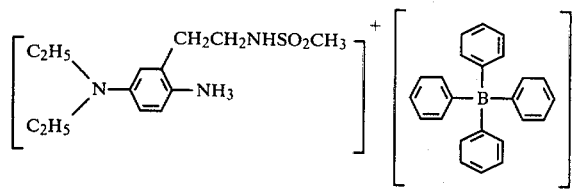 |
| NB-17 | 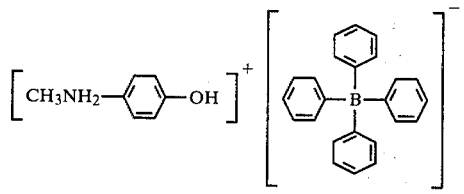 |
| NB-18 | 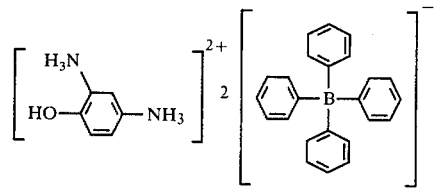 |
| NB-19 | 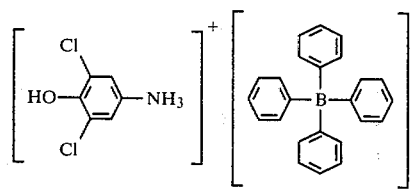 |

-continued
| Nos. | Chemical formulae |
|---|---|
| NB-20 | 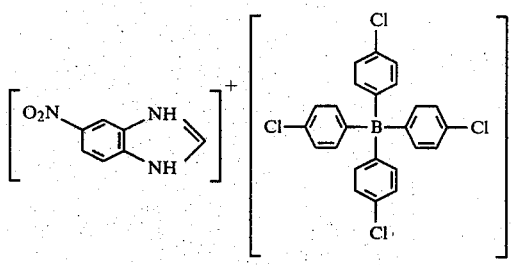 |
| NB-21 | 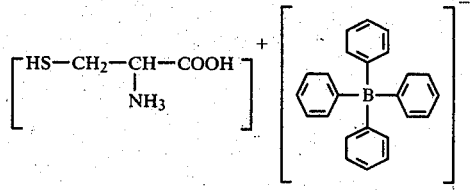 |
| NB-22 | 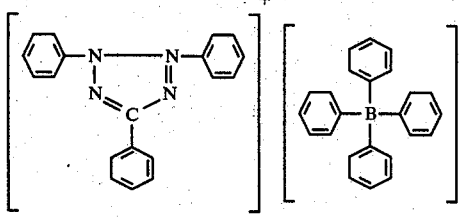 |
| NB-24 | 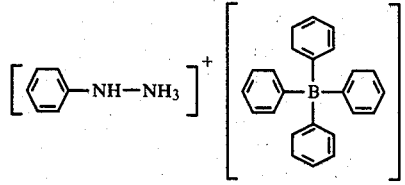 |
| NB-25 | 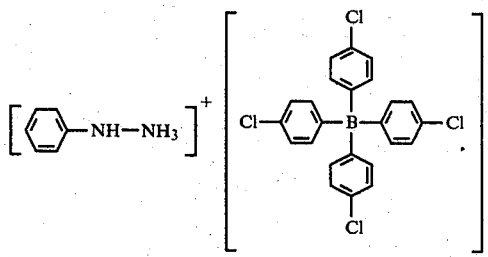 |
| NB-26 | 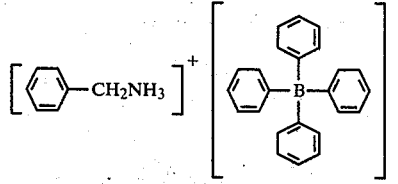 |
| NB-27 | 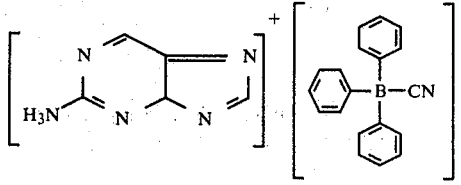 |

| Nos. | Chemical formulae |
|---|---|
| NB-28 | $[NH_3OH]^+ \; [B(C_6H_5)_4]^-$ |
| NB-29 | [isoquinolinium-N-CH$_2$-C$_6$H$_5$]$^+$ [B(C$_6$H$_5$)$_4$]$^-$ |
| NB-30 | $\left[ (C_2H_5)_2N\text{-}C_6H_4\text{-}NH_3 \right]^+ \; \left[ (C_4H_9)_4B \right]^-$ |
| NB-31 | $\left[ \begin{array}{c} C_2H_5 \\ CH_3SO_2NH(CH_2)_2 \end{array} \!\!N\text{-}C_6H_4\text{-}NH_3 \right]_3^{3+} \; [B(C_6H_5)_4]_3^-$ Wait, formatted: $\left[ \begin{array}{c} C_2H_5, CH_3O(CH_2)_2 \end{array}NH\text{-}C_6H_4\text{-}NH_3 \right]^{3+}_3 [B(C_6H_5)_4]^-_3$ |
| NB-32 | $\left[ \begin{array}{c} C_2H_5, CH_3O(CH_2)_2 \end{array}NH\text{-}C_6H_3(CH_3)\text{-}NH_3 \right]^{2+}_2 [B(C_6H_5)_4]^-_2$ |
| NB-33 | $\left[ \begin{array}{c} C_2H_5, HO(CH_2)_2 \end{array}NH\text{-}C_6H_3(CH_3)\text{-}NH_3 \right]^{2+}_2 [B(C_6H_5)_4]^-_2$ |
| NB-34 | $\left[ (C_2H_5)_2N\text{-}C_6H_3((CH_2)_2NH SO_2CH_3)\text{-}NH_3 \right]^{3+}_3 [B(C_6H_5)_4]^-_3$ |

For example, the said compound NB-1 is composed according to the following reaction formula:

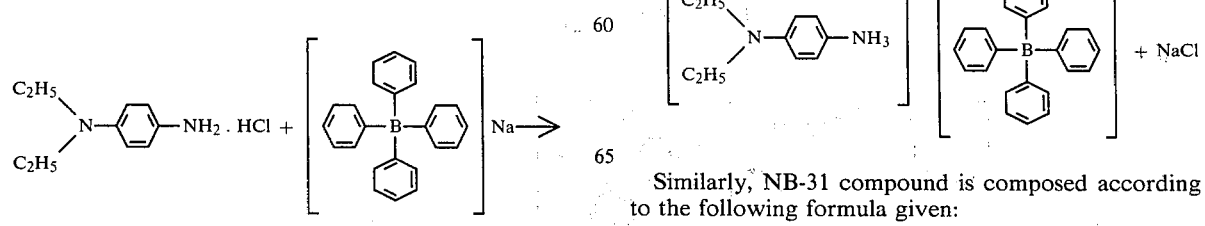

+ NaCl

Similarly, NB-31 compound is composed according to the following formula given:

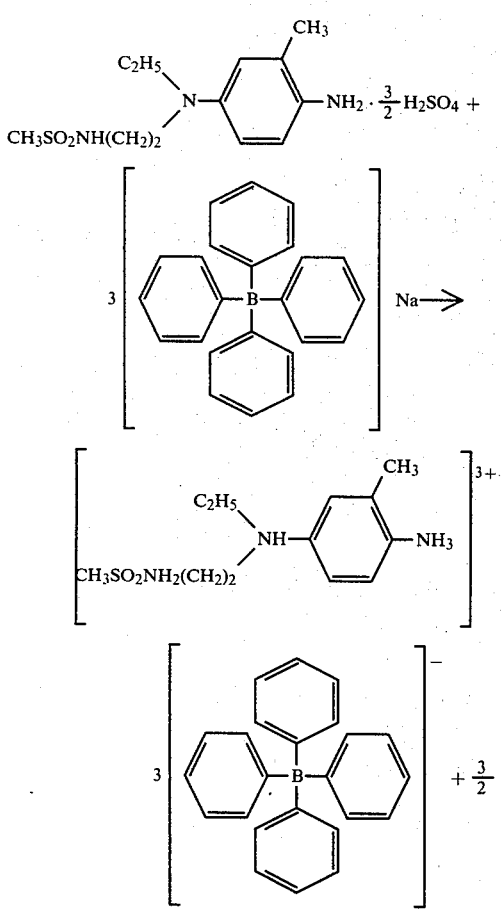

In making the said reaction in aqueous solvent, crystals which are inhibitive to be dissolved in water are deposited and the objective can easily be obtained, and recrystallization is possible by making use of water, methylalcohol or ethylalcohol, etc. And the objective can be refined by adding with n-hexane and then by precipitating after dissolving with acetone or chloroform. In the event that the objective cannot be obtained in a crystal form, it may be possible to extract the objective from resulted water solution by making use of ethylacetate, ether or chloroform, etc.

And, as the case may be, after dissolving ammonia, nitrogen containing organic base or quaternary nitrogen atom and boron compound into water separately from each other, both solutions are mixed in gelatin solution while stirring together, and thus the objective can be obtained in a state that the objective is dispersed in gelatin solution, and the said method may rather be preferable in case that the objective is hard to be crystallized. This may also be preferable in case of adding it into photographic material because the treating becomes easier.

The most preferable method for preparing compound used in the invention is that making salts such as hydrochloric acid, sulfuric acid, phosphoric acid, nitric acid or p-toluenesulfonic acid, etc. having nitrogen containing organic base react with lithium salt or sodium salt of boron compound, both in water solvent. In case that ammonia or nitrogen containing organic base is a free base, it is necessary for making a reaction to add an enough quantity of inorganic acid such as hydrochloric acid, sulfuric acid, phosphoric acid and nitric acid, etc. or organic acid such as benzenesulfonic acid and p-toluenesulfonic acid, etc. to make a reaction. Compound containing quaternary nitrogen atom may be as good as reacted with sodium salt or lithium salt of boron compound in water solution.

The following are the typical examples for obtaining the said compound:

[SYNTHESIS EXAMPLE 1]

Synthesis of compound NB-1

35 g of sodium tetraphenylborate are dissolved in 700 ml of water and then they are stirred with keeping temperature at approx. 5° C. 20 g of 4-amino-N,N-diethylaniline hydrochloride, which is dissolved in 250 ml of water, are dropped into the said aqueous solution of sodium tetraphenylborate for about 30 minutes, and then they are stirred for about an hour. After filtered and dried, the deposited crystals are recrystallized from water-methanol mixed solvent (85% of methanol), and then 25 g of purple-rose colored powdered crystals are obtained. Melting point at 96°–99° C.

The structure of compound in the Compound Example NB-1 is supported by nuclear magnetic resonance spectrum (NMR spectrum).

[SYNTHESIS EXAMPLE 2]

Synthesis of compound NB-4

Except that, in the Synthesis example 1, 35 g of sodium tetraphenylborate is replaced by 41 g of sodium tetra-p-tolyl borate and 20 g of 4-amino-N,N-diethylanilinehydrochloride is replaced by 22 g of 4-amino-3-methyl-N,N-diethyl aniline hydrochloric acid salt, 35 g of pink-colored powdered crystals are obtained in exactly same manner as the synthesis example 1. Melting point is at 107° C.

The structure of the compound 4 is supported by NMR spectrum.

[SYNTHESIS EXAMPLE 3]

Synthesis of compound NB-10

Except that, in the Synthesis example 1, 20 g of 4-amino-N,N-diethylaniline hydrochloride is replaced by 44 g of 4-amino-3-methyl-N-ethyl-N-[β-(methylsulfonamido)ethyl]aniline 3/2 sulfate monohydrate, 25 g of purple-rose-colored powdered crystals are obtained in the exactly same way as the Synthesis example 1. Melting point is at 148°–151° C.

The structure of the compound NB-10 is supported by NMR spectrum.

[SYNTHESIS EXAMPLE 4]

Synthesis of compound NB-3

49 g of sodium tetra-p-chlorophenylborate is dissolved in 1 l of water and then 22 g of 4-amino-3-methyl-N,N-diethylaniline hydrochloride, which are dissolved in 250 ml of water with keeping temperature of about 5° C., are dropped into the said aqueous solution for approx. 30 minutes, and then they are stirred for about an hour. After filtered and dried, deposited crystals are dissolved in 300 ml of chloroform and crystals are made deposit by adding 1 l of n-hexane with stirring, then, 32 g of purple-rose-colored powdered crystals are obtained. Melting point is at 54°–60° C.

The structure of compound NB-3 is supported by NMR spectrum.

[SYNTHESIS EXAMPLE 5]

Synthesis of compound NB-9

70 g of sodium tetraphenylborate is dissolved in 700 ml of water and then 22 g of N,N,N',N'-tetramethyl-p-phenylenediamine dihydrochloride, which are dissolved in 250 cc of water with keeping temperature of approx. 5° C., are dropped into the said aqueous solution for approx. 30 minutes and then they are stirred for about a couple of hours. After filtered and dried, deposited crystals are recrystallized from water-methanol mixture solvent (90% of methanol), and then 35 g of blue-purple-colored crystals are obtained. Melting point is at 129°–132° C.

The structure of compound NB-9 is supported by NMR spectrum.

[SYNTHESIS EXAMPLE 6]

Synthesis of compound NB-20

49 g of sodium tetra-p-chlorophenylborate is dissolved in 1 l of water, and then 23 g of 5-nitro-benzimidazole nitrate, which are dissolved in 500 ml of water with keeping temperature of approx. 10° C., are dropped in the said aqueous solution for approx. 30 minutes and then the mixture is stirred for about an hour. After filtered and dried, deposited crystals are dissolved in 300 ml of chloroform and crystals are deposited by adding 1 l of n-hexane with stirring, and then 30 g of white powdered crystals are obtained. Melting point is at 138°–143° C.

The structure of compound NB-20 is supported by NMR spectrum.

[SYNTHESIS EXAMPLE 7]

Synthesis of compound NB-21

Except that, in the composition example 1, 20 g of 4-amino-N,N-diethylanilinehydrochloride is replaced by 16 g of L-cysteinehydrochloride, 24 g of white powdered crystals are obtained in the exactly same way as the Synthesis example 1. Melting point is at 60°–65° C.

The structure of compound NB-21 is supported by NMR spectrum.

[SYNTHESIS EXAMPLE 8]

Synthesis of compound NB-25

Except that, in the Synthesis example 4, 22 g of 4-amino-3-methyl-N,N-diethylanilinehydrochloride is replaced by 15 g of phenylhydrazinehydrochloride, 24 g of white powdered crystals are obtained in the exactly same way as example 4. Melting point is at 65°–70° C.

The structure of the compound NB-25 is supported by NMR spectrum.

[SYNTHESIS EXAMPLE 9]

Synthesis of compound NB-17

8 g of N-methyl-p-aminophenylhydrochloride is dissolved in 500 ml of 15% gelatin aqueous solution and then 18 g of tetraphenyl borate diluted by 500 ml of water is added gradually into the above solution with stirring. After cooling the said gelatin solution thus obtained, they are cut in a noodle shape, washed well with cold water and then refined.

The compound is added to hydrophilic colloid, which is coated on a support to form a photographic layer. The compound is dispersed in hydrophilic colloidal solution in such a way that the compound is dissolved in hydrophilic organic solvent (e.g. methylalcohol, ethylalcohol, acetone, etc.), then added to the colloidal solution, or may be dispersed in hydrophilic colloidal solution by the method using latex or other polymer or by the dispersion method of oil/water emulsifying. As for oil to be used for the oil/water emulsifying dispersion method, oil for use of coupler dissolving. For example, tri-o-cresylphosphate, trihexylphosphate, dioctylbutylphosphate, dibutylphthalate, diethyllaurylamido, 2,4-diarylphenol, benzoic octyl, etc. are given. Compound obtained by a synthesis method in a gelatin solution, e.g. Synthesis Example 9 may be added directly to the hydrophilic colloid.

To disperse such oil which dissolves the compound in water phase, usually a surface active agent is used. For example, anionic surface active agents containing acid group such as carboxylic acid, sulfonic acid, phosphoric acid, sulfuric ester, phosphoric ester group, etc., and nonionic or cationic or amphoteric surface active agent, are used.

As for hydrophilic colloids, those which are well known as a binder for photographic use are used. For example, gelatine, gelatin derivatives, graft polymers of gelatin and other polymer, cellulose derivatives such as hydroxyethyl cellulose, carboxymethyl cellulose, cellulose sulfonic acid ester, etc., sodium alginate, starch derivatives, and a variety of composed hydrophilic macromolecule substance such as monomer or copolymer of polyvinyl alcohol partial acetal, poly-N-vinylpyrolidone, polyacrylic acid, polymethacrylic acid, polyacrylamido, polyvinylimidazole, polyvinylpyrazole, etc., any of which can be used. Or latex and so on can also be added in. As for example, the compounds described in the U.S. Pat. No. 3,518,088 and No. 148-14850 of the Research Disclosure, issued in August, 1976, are given therefor.

In case that the compound having nitrogen organic base or quaternary nitrogen atom is a developing agent, the compound of the present invention works as a precursor for a color developing agent. Examples of the precursor are NB 1–8, 10–16 and 30–34, in which NB 1–8, and 10–16 are preferable. Practically NB 2 and 5 are most usable.

An antioxidizing agent or stabilizing agent for photographic use, which has been well known, is preferably added in the layer containing the compound of the present invention. For example, reductons such as hydroquinone derivatives and ascorbic acid, etc., hydroxylamines, sulfonylic compounds, active methylene compounds, etc. are given for the agent.

The coating volume of color developing agent precursor to be used for the photographic material of the invention is at 0.1–10 mol, preferably at 0.25–5 mol to the total silver amount of the photographic material. The color developing agent precursor can be included in light-sensitive layer containing silver halide emulsion or in other layer than the above. The said precursor is preferably included in other layer than a light-sensitive layer.

In comparison with the conventional developing process, the developing process of photographic material in the invention has only a different point that the color developing bath is an alkaline activating bath, and the other processes can be applied as they are used in the conventional processes.

pH of the said activating bath is within the range of 7–14, particularly the range of approximately 8–13 is preferable. Temperature of the activator bath is selected within the range of 20° C.–70° C., but preferably at 30° C.–60° C.

The activator for use in the invention is substantially a conventional color developing solution from which a developing agent is removed. As for activator buffering agent, etc., sodium hydroxide, potassium hydroxide, sodium carbonate, potassium carbonate, tertiary sodium phosphate or tertiary potassium phosphate, potassium metaborate, borax, etc. are used individually or combinedly. And for the purposes of giving buffering ability, convenience for preparation or making ionic strength stronger, etc., a variety of salts such as disodium hydrogen phosphate or dipotassium hydrogen phosphate, sodium dihydrogen phosphate or potassium dihydrogen phosphate, sodium bicarbonate or potassium bicarbonate, boric acid, alkali nitrate, alkali sulfate, etc., may be used.

And an appropriate quantity of fog restraining agent may further be contained. As for the said restraining agents, inorganic halide compounds and organic anti-fogging agents which have already been known are given as the examples. As the representative examples of the said inorganic halide compounds, such the bromides as sodium bromide, potassium bromide or sodium iodide, and such the iodides as potassium iodide or sodium iodide, are given. On the other hand, as for the examples of organic anti-fogging agents, 6-nitrobenzindazole, described in the U.S. Pat. No. 2,496,940, 5-nitrobenzimidazole described in the U.S. Pat. No. 2,656,271, diaminophenazine described in the Journal of the Society of Photographic Science and Technology of Japan, vol. 11, page 48 (1948), o-phenylenediamine, and further hetero cyclic compounds represented by mercaptobenzimidazole, methylbenzthiazole, mercaptobenzoxazole, thiouracyl, 5-methylbenztriazole, and the compound described in the Japanese Patent Publication No. 46-41675, are given. Besides, as for anti-fogging agents, the one described in the Kagaku Shashin Binran vol. 2, page 119 (published by Maruzen Book Co. in 1959) can also be used.

In order to control surface layer development, the development restraining agents, which have been known by the Japanese Patent Publication Nos. 46-19039 and 45-6149, and the U.S. Pat. No. 3,295,976 and so on, can also be used.

Besides, ammonium chloride, potassium chloride, sodium chloride, etc. can also be added as occasion calls. And any of development accelerating agent can further be added if necessary. Among the above development accelerating agents, the following are included; a variety of pyridium compounds as represented by those described in the U.S. Pat. No. 2,648,604, the Japanese Patent Publication No. 44-9503, the U.S. Pat. No. 3,671,247; other cationic compounds; cationic dyes such as phenosafran; polyethyleneglycol and its derivatives as described in the Japanese Patent Publication No. 44-9504, the U.S. Pat. Nos. 2,533,990, 2,531,832, 2,950,970, and 2,577,127, nonionic compounds such as polythioethers, etc., organic solvents as described in the Japanese Patent Publication No. 44-9509 and the Belgian Pat. No. 682,862, organic amine, ethanolamine, ethylenediamine, diethanolamine, etc. Further, the accelerating agent described at length in the pages 40–43 of "Photographic Processing Chemistry", by L. F. A. Mason, (published by Focal Press, London in 1966) is also included.

Furthermore, benzylalcohol as described in the U.S. Pat. No. 2,304,925, phenethylalcohol, pyridine as described in Journal of the Society of Photographic Science and Technology of Japan, vol. 14, 74 (1952), ammonia, hydrazine, amines, etc. can be effective development accelerating agents if suitable for a specific purpose.

Besides, sodium sulfite, potassium sulfite, potassium bisulfite or sodium bisulfite can be added therewith.

And further, polyphosphoric compounds represented by sodium hexamethaphosphate, sodium tetrapolyphosphate, sodium tripolyphosphate or potassium salts of each of the above polyphosphoric acids, and, aminopolycarbonic acids represented by ethylenediamine tetraacetic acid, nitrilotriacetic acid, cyclohexandiaminetetraacetic acid, iminodiacetic acid, N-hydroxymethyl, ethylenediamine triacetic acid, diethylenetriaminepentaacetic acid, etc., every one of which can be used as water softener. An adding quantity of the said water softner depends upon hardness of water, but approx. 0.5–10 g/l are normally used. Other calcium or magnecium hiding agent can also be used. Those facts as mentioned above are fully described in "Belgisches Chemiches Industry", vol. 21, page 325 (1956) and vol. 23, page 1105 (1958), both by J. Willems.

If occasion demands, some organic solvent can be contained.

Among the above organic solvents, the following are included; ethyleneglycol, hexyleneglycol, diethyleneglycol, methylcellosolve, methanol, ethanol, acetone, triethyleneglycol, dimethylformaldehyde, dimethylsulfoxide and also compounds as described in the Japanese Patents Publication Nos. 47-33378 and 44-9509.

The adding quantity of the said organic solvent can be varied in accordance with component structure of activators, but the quantity is less than 50% of solution to be used, and normally less than 10% of it. However, some of composed solvents may contain almost no water, sometimes.

As for adjunct developing chemicals, N-methyl-p-aminophenolhemisulfate (so-called metol), benzyl-p-aminophenol hydrochloride, N,N-diethyl-p-aminophenol hydrochloride, p-aminophenolsulfate, 1-phenyl-3-pyrazolidone (phenidone), N,N,N',N'-tetramethyl-p-phenylenediamine hydrochloride, etc., can be used. The preferable adding quantity of the above adjunct developing chemical is normally 0.01–1.0 g/l.

Besides, the following, for example, are added in activating solution, if occasion demands.

As for competing couplers (colorless couplers) such as citrazinic acid, J acid and H acid, those as described in the Japanese Patents Publication Nos. 44-9505, 44-95-6, 44-95-7, 45-14036 and 44-9508, and the U.S. Pat. Nos. 2,742,832, 3,520,690, 3,560,212 and 3,645,737, etc., are given.

As for fogging agents such as alkaline metallic hydride, aminoborane and ethylenediamine, those as described in the Japanese Pat. No. 47-38816, etc., are given.

The said nitrogen containing organic base, for example, 5-nitrobenzimidazole, o-phenylene diamine, N-methyl-p-aminophenol or N,N,N',N'-tetramethyl-p-phenylenediamine, etc., can be contained in a desired layer of light-sensitive material as a stable and immobile or non-diffusible compound by applying with the method of this invention, thereby composite of alkaline activator can be made lessen to the utmost. This not only makes the process simple and chemical disposal extremely less, but also this is advantageous from the aspect of environmental pollution.

The compounds, which are built in photographic material of this invention and which contain with ammonia or nitrogen containing organic base or quaternary nitrogen atom, are not active in storage of light-sensitive material, so they have no influence upon light sensitive material, but are active only when alkaline activator is applied with, therefore, the light-sensitive material can be stored stably and satisfactory photographic image can be obtained by making use of simply composed alkaline activator.

In such a light-sensitive material that a compound producing dye by making reaction with oxidized developing agent, so-called a coupler, is contained in a light sensitized photographic emulsion layer, the compound that is the objective of the invention can be contained in the said emulsion layer or other layer.

The composition as mentioned above is of especially advantageous embodiment of the invention. The above mentioned coupler has such a composition as not to diffuse to other layer during a process of manufacturing or processing.

As for yellow couplers, open-chain-diketomethylene compounds are widely used. As for magenta couplers, 5-pyrazolone compound is mainly used as well as indazolone compounds and cyanoacetyl compounds. As for cyan couplers, derivatives of phenol or naphthol are mainly used.

Besides, in color reaction, such the compound, that discharges development Inhibitor Releasing type coupler (so-called DIR coupler) and development inhibiting compound, can be added.

In order to satisfy the characteristics required for light sensitive material, more than two kinds of the above couplers can be applied together onto a certain single layer and it is of course all right to add the same compound onto more than two different layers.

It is desirable that the coupler is the one that does not dissolve in water mixed with coupler solvent (preferably the coupler solvent with a proper polarity). As a useful typical solvent, tri-o-cresylphosphate, dibutylphthalate, diethyllaurylamido, 2,4-diallylphenol and liquid dye stabilizing agent.

The compound used in the photographic light-sensitive material of this invention can be applied either to general silver halide color photographic material such as color negative film, color paper, color positive film and color reversal film, etc. or to direct positive type silver halide color photographic material. Furthermore, it can be applied to black and white silver halide photographic material as well as to the coupler for forming black dye, and in this case the reduction of silver halide is possible.

Further, it can be used in the diffusion transfer color photography method that is similar to the method described in the specifications of U.S. Pat. Nos. 3,227,551 and 3,227,552.

In case the nitrogen atom containing organic base used for obtaining the compound that is used in this invention has the functions of black and white developing agent, inhibitor, development accelerator, toning agent or sensitizer, etc., it can aslo be applied to black and white silver halide photographic light-sensitive material.

The photographic light-sensitive material of this invention can be a color photographic light-sensitive material with lower silver amount described in the specifications of U.S. Pat. Nos. 3,765,891 and 4,094,682, and in this case, the photographic light-sensitive material of this invention is processed in the intensifying bath that contains trivalent cobalt complex or hydrogen peroxide.

The silver halide emulsion to be used in the photographic light-sensitive material of this invention is ordinarily prepared by mixing water-soluble silver salt (e.g. silver nitrate) solution and water-soluble halogen salt (e.g. potassium bromide) solution under the existence of water-soluble high polymer solution such as gelatin. As such silver halide, a mixed silver halide such as silver chloro-bromide, silver iodo-bromide and silver chloro-iodo-bromide, etc. can be used besides silver chloride and silver bromide.

Above-mentioned silver halide emulsion may be chemically sensitized by an ordinary method. It is possible to add an antifoggant of silver halide in the light-sensitive layer of photographic light-sensitive material. A useful typical anti-foggant includes heterocyclic organic compound such as tetrazole, azaindene and triazoles, aromatic compound that has mercapto group or heterocyclic compound.

The layer of the photographic light-sensitive material of this invention may include hardening agent, plasticizer, lubricant, surface active agent, brightening agent and other additives used ordinarily in the field of photographic technology.

Photographic emulsion, as occasion demands, can be given spectral sensitization or super-sensitization by a single or combined use of cyanine dyes such as cyanin, merocyanine, and hemicyanin or by the combined use of cyanine dyes and styryl dye.

This photographic emulsion is coated onto the flat material that does not make a remarkable dimensional change during processing such as a hard support like glass, or a flexible support, according to the purpose.

The light-sensitive material of this invention may, at request, contain more or less compound containing ammonia or nitrogen atom containing organic base or quaternary nitrogen atom to be used to obtain compounds which are used in this invention, than chemically equivalent quantity needed for reaction against boron compound and the most preferable embodiment of this invention is the case in which the compound and boron compound containing ammonia or nitrogen atom containing organic base or quaternary nitrogen atom, having the same mol number in the viewpoint of chemical equivalent quantity are contained in the light-sensitive material.

Further, compounds to be used in this invention can be used singly or can be used jointly with more than two kinds and when aromatic primary amine developing agent and hydrazine fogging agent are contained in the direct positive type silver halide color photographic light-sensitive material in accordance with a conventional method, it is possible to obtain a reversal color image directly by treating the direct positive type silver halide color photographic light-sensitive material with alkali activator alone, which produces a big advantage on simplification of processing and stabilization of preservation of processing liquid.

Regarding the processing method for the light-sensitive photographic material of this invention, the processing by soaking in the bath as usual method is possible as a matter of course and the processing by other known method is also fairly possible.

So-called spray method to process by atomizing processing liquid, or web method to process by overlapping the carrier containing processing liquid on the light-sensitive material, or further a method to coat viscous processing liquid on the surface of the light-sensitive material, can be adopted.

This invention will further be explained in detail with examples as follows.

[EXAMPLE 1]

As a precursor of color developing agent, 6 g of the compound NB-10 was added to the mixed liquid of dibutylphthalate 6 ml and ethylacetate 20 ml and was dissolved completely at 40° C. This solution was mixed with 5 ml of 10% water solution of alkanol B (alkyl-naphthalensulfonate, made by E. I. du Pont de Nemours & Co.) and 200 ml of 5% water solution of gelatin and was emulsified and dispersed by means of a colloid mill and dispersion liquid of a precursor of color developing agent was prepared to be finished to 330 ml by adding water, coating aid and hardening agent. The liquid obtained in this way was coated on the resin-coated paper support. The coating amount per 100 cm² of the precursor used in this occasion was 4.0 mg. On this layer, 2-[2-(2,4-di-t-pentylphenoxy)butaneamido]-4,6-dichloro-5-methylphenol was dissolved in dibutylphthalate as a coupler and then was protect dispersed in the aqueous solution of gelatin and was coated and dried after mixing with red-sensitive silver chloro-bromide emulsion. The coating amount per 100 cm² of the coupler used on this occasion was 3.0 mg and the amount of silver was 2.1 mg.

Further on this layer, the aqueous solution with 3% of gelatin was coated in order to form a protection layer. The coating aid and hardening agent were contained in each layer. The sample obtained in this way was designated as sample 1. The sample obtained in exactly the same manner as the sample 1 except that the precursor of color developing agent was changed to the compound (A) 3.6 g represented by the following structural formula, was designated as sample 2.

Similarly, the sample obtained by using the compound (B) 4.8 g as the precursor of color developing agent, was designated as sample 3.

Compound (A)

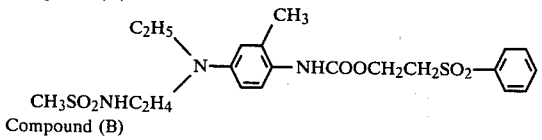

Compound (B)

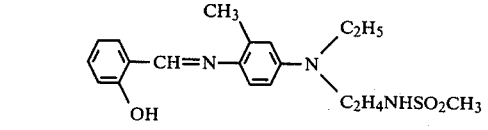

(Compound (A) described in the Japanese Patent L-O-P publication No. 53-135628 and compound (B) described in the U.S. Pat. No. 3,342,599 were used for comparison.)

The white light exposure was given to sample 1, sample 2 and sample 3 through the step wedge and then the following processing was given thereto.

| Processing step | | |
| --- | --- | --- |
| Activator development | 50° C. | 1 minute |
| Bleach-fix | " | 1.5 minutes |
| Washing | " | 2 minutes |
| Stabilization | " | 1 minute |
| Activator liquid | | |

| -continued | |
| --- | --- |
| Benzyl alcohol | 14 ml |
| Sodium sulfite | 2 g |
| Potassium bromide | 0.5 g |
| Sodium carbonate (monohydrate) | 30 g |
| Add water to make | 1 l |
| Bleach-fix bath | |
| Ammonium thiosulfate (70%) | 150 ml |
| Sodium sulfite | 5 g |
| Na[Fe(III) (EDTA)] | 40 g |
| EDTA | 4 g |
| Add water to make | 1 l |
| (EDTA: ethylene diamine tetra acetic acid) | |
| Stabilizing liquid | |
| Glacial acetic acid | 10 ml |
| Sodium acetate | 5 g |
| Formalin (37%) | 5 ml |
| Add water to make | 1 l |

Results obtained are shown in table 1.

Incubation test was given to sample 1, sample 2 and sample 3 by preserving them in the air at 50° C. for two days and then the aforesaid exposure and processing were given to each of them. Results obtained are shown in table 1.

TABLE 1

| Sample number | Compound | fog | Relative sensitivity | Maximum density |
| --- | --- | --- | --- | --- |
| Sample 1 (this invention) | NB - 10 | 0.05 | 100 | 2.40 |
| Sample 2 (other than this invention) | Compound A | 0.05 | 56 | 1.18 |
| Sample 3 (other than this invention) | Compound B | 0.39 | 49 | 1.87 |
| After forced deterioration test | | | | |
| Sample 1 (this invention) | NB - 10 | 0.05 | 98 | 2.38 |
| Sample 2 (other than this invention) | Compound A | 0.07 | 52 | 1.03 |
| Sample 3 (other than this invention) | Compound B | 0.53 | 38 | 1.21 |

Note
The relative sensitivity means a relative sensitivity against a sensitivity of 100 of sample 1 (which was not given a forced deterioration test)

Compounds (A) and (B) used for a comparison are considered to be most excellent among the known color developing agent containing technologies, but the compound (A) had a low sensitivity and a maximum color density was low, although the fog thereof was low. The compound (B) itself is colored yellow and its defect that the light-sensitive material processed becomes the one with a high yellow fog unless the precursor is decomposed by alkali, was noticed. Further, it is found from the forced deterioration test that the sample 3 containing the compound (B) is not very good in secular stability.

However, the sample 1 that is a photographic light-sensitive material of this invention has a low fog and a high sensitivity and is greatly excellent in color density and badness of secular stability which is the biggest defect of the color developing agent containing type light-sensitive material has been completely solved.

[EXAMPLE 2]

As a coupler, 2-(1-benzyl-2,4-dioxyimidazolidine-3-yl)-2-pivallyl-2'-chloro-5'-[4-(2,4-di-t-pentylphenoxy)-butaneamido]acetanilide was dissolved in dibutylphthalate and after the protect dispersing in gelatin water solution, it was mixed with silver chloro-bromide emulsion and was coated on the resin-coated paper support. The coating amount per 100 cm² for coupler and silver used on this occasion was 8.3 mg for coupler and 3.5 mg for silver. Onto this, dioctylhydroquinone and compound NB-2, after being dissolved in tricresylphosphate and after the protect dispersing in gelatin water solution, were coated. The coating amount per 100 cm² for dioctylhydroquinone and compound NB-2 was 0.9 mg for dioctylhydroquinone and 10.0 mg for compound NB-2.

Furthermore, onto this, 3-{2-chloro-5-[1-(octadecyl)-succinimido]anilino}-1-(2,4,6-trichlorophenyl)-5-pyrazolone was dissolved in dibutylphthalate and after the protect dispersing in gelatin water solution, it was mixed with green-sensitive silver chlorobromide emulsion and coated and dried. The amount of coupler used on this occasion was 4.3 mg per 100 cm² and the amount of silver was 3.9 mg.

On this layer, dioctylhydroquinone and compound NB-2, after being dissolved in tricresylphosphate and after the protect dispersing in gelatin water solution, were mixed with silver chloro-bromide emulsion and were coated. The coating amount per 100 cm² for coupler and silver used on this occasion was 8.3 mg for coupler and 3.5 mg for silver. Onto this, dioctylhydroquinone and compound NB-2, after being dissolved in tricresylphosphate and after the protect dispersing in gelatin water solution, were coated. The coating amount per 100 cm² for dioctylhydroquinone and compound NB-2 used on this occasion was 0.9 mg for dioctylhydroquinone and compound NB-2 used on this occasion was 0.5 mg for dioctylhydroquinone and 7.0 mg for compound NB-2. Further onto this layer, 2-[2-(2,4-di-t-pentylphenoxy)butaneamido]-4,6-dichloro-5-methylphenol was dissolved in dibutylphthalate as a coupler and after the protect dispersing in gelatin water solution, it was mixed with red-sensitive silver chlorobromide emulsion and was coated and dried. The coating amount per 100 cm² for the coupler used on this occasion was 3.0 mg and the amount of silver was 2.1 mg.

Onto this layer, compound NB-2, after being dissolved in tricresylphosphate and after the protect dispersing in gelatin water solution, was coated. The coating amount per 100 cm² for compound NB-2 used on this occasion was 3.5 mg. The sample obtained in this way was designated as sample 4.

The sample obtained by using compound NB-3 instead of compound NB-2 was designated as sample 5.

Likewise, sample 6 was obtained by using compound NB-11, sample 7 by using compound NB-32 and sample 8 by using compound NB-33.

Furthermore, sample 9 was obtained by using compound (A) used in example 1 and sample 10 was obtained by using compound (B), as a comparison sample. For each compound, however, the coating amount was varied so that the mol number for each compound equalled that of compound NB-2. Samples 4–10 were given a white light exposure and were processed in exactly the same manner as example 1. Results obtained therefrom are shown in table 2.

TABLE 2

| Sample number | Compound | Fog | | | Note 1 Relative sensitivity | | | Maximum density | | |
|---|---|---|---|---|---|---|---|---|---|---|
| | | Y | M | C | Y | M | C | Y | M | C |
| Sample 4 (this invention) | NB-(2) | 0.07 | 0.06 | 0.05 | 100 | 109 | 107 | 2.41 | 2.46 | 2.38 |
| Sample 5 (this invention) | NB-(3) | 0.06 | 0.07 | 0.05 | 98 | 103 | 102 | 2.27 | 2.31 | 2.25 |
| Sample 6 (this invention) | NB-(11) | 0.05 | 0.06 | 0.07 | 94 | 98 | 99 | 2.36 | 2.39 | 2.29 |
| Sample 7 (this invention) | NB-(32) | 0.07 | 0.08 | 0.05 | 97 | 106 | 101 | 2.31 | 2.36 | 2.34 |
| Sample 8 (this invention) | NB-(33) | 0.05 | 0.07 | 0.06 | 95 | 105 | 101 | 2.31 | 2.44 | 2.37 |
| Sample 9 (other than this invention) | (A) | 0.09 | 0.09 | 0.06 | 63 | 79 | 62 | 0.91 | 1.59 | 0.81 |
| Sample 10 (other than this invention) | (B) | 1.98 | 0.50 | 0.29 | — | — | 48 | 2.02 | 1.58 | 1.79 |
| After forced deterioration | | | | | | | | | | |
| Sample 4 (this invention) | NB-(2) | 0.07 | 0.07 | 0.07 | 98 | 107 | 107 | 2.40 | 2.41 | 2.38 |
| Sample 5 (this invention) | NB-(3) | 0.06 | 0.08 | 0.06 | 97 | 103 | 98 | 2.25 | 2.33 | 2.19 |
| Sample 6 (this invention) | NB-(11) | 0.05 | 0.08 | 0.07 | 93 | 97 | 98 | 2.34 | 2.37 | 2.25 |
| Sample 7 (this invention) | NB-(32) | 0.07 | 0.09 | 0.06 | 97 | 103 | 97 | 2.36 | 2.32 | 2.24 |
| Sample 8 (this invention) | NB-(33) | 0.08 | 0.07 | 0.06 | 94 | 101 | 101 | 2.29 | 2.45 | 2.35 |
| Sample 9 (other than this invention) | (A) | 0.13 | 0.12 | 0.09 | 58 | 73 | 56 | 0.83 | 1.39 | 0.74 |
| Sample 10 (other than this invention) | (B) | 2.03 | 0.68 | 0.34 | Note 2 | — | 42 | 2.03 | 1.01 | 1.03 |

Note 1 Figures in "relative sensitivity" column show the relative sensitivity against 100 of sensitivity for yellow of the sample 4 (which was not given the test of forced deterioration).
Note 2 It is shown by "m" that the measurement was impossible due to the high fog.

The table 2 shows that the sample 9 for the use of comparison has a low fog but the sensitivity and the maximum density especially those for yellow and cyan are extremely low. As for the sample 10 for the use of comparison, on the other hand, the fog for yellow of the light-sensitive material is extremely high because the compound (B) itself is yellow and subsists in the light-sensitive material without being separated by alkali. As for the samples 4, 5, 6, 7 and 8 of the light-sensitive material of this invention, however, it is shown that the fog is low and the sensitivity and the maximum density are very high and a decrease in the increased sensitivity of the fog and the decline in the maximum density after the test of forced deterioration are smaller than the samples for the use of comparison.

[EXAMPLE 3]

As a coupler for forming black dye, 10 g of N-octadecyl-m-aminophenol was added to the mixed solution of 10 ml of tricresylphosphate and 30 ml of ethyl acetate and was dissolved completely at 50° C. This solution was mixed with 5 ml of 10% water solution of alkanol B and 200 ml of 5% water solution of gelatin and was emulsified by a colloid mill to prepare coupler-dispersed liquid. This coupler-dispersed liquid was added to 500 g of silver iodo-bromide emulsion for the use of X-ray (including silver iodo-bromide of 5 mol%) and it was coated on one side of polyester base so that the silver amount was 40 mg/100 cm$^2$. On this layer, the compound NB-2 was coated after it was dissolved in tricresylphosphate and was protect-dispersed in gelatin water solution. The coating amount per 100 cm$^2$ of the compound NB-2 used then was 20 mg. (sample 11).

As a comparison, on the other hand, mere gelatin water solution that does not contain the compound NB-2 was coated on the sample on which silver iodo-bromide emulsion for the use of X-ray containing the said coupler for forming black dye was coated. (sample 12).

Sample 11 is an X-ray light-sensitive material that contains the precursor of the color developing agent of this invention and coupler for forming black dye and sample 12 is an X-ray light-sensitive material that contains only coupler for forming black dye.

After the wedge exposure was given to sample 11, it was developed with alkali activator with following composition at 20° C. for 5 minutes and then was given an ordinary fixing and washing.

| Sodium sulfite unhydride | 10 g |
|---|---|
| Sodium carbonate 1 H$_2$O | 30 g |
| Potassium bromide | 0.5 g |
| Add water to make | 1 l |

Meanwhile, the sample 12 that was exposed in the same manner was developed in the developer with following composition at 20° C. for 5 minutes and then was given an ordinary fixing and washing.

| 4-amino-3-methyl-N,N-diethyl-anilinehydrochloride | 2 g |
|---|---|
| Sodium sulfite unhydride | 10 g |
| Sodium carbonate 1 H$_2$O | 30 g |
| Potassium bromide | 0.5 g |
| Add water to make | 1 l |

After processing, both sample 11 and sample 12 had dye image and silver image and sample 11, compared with the control sample 12, showed the equal photographic properties on all the points of fog, sensitivity and maximum density.

Alkali activator used to process sample 11 and the developer used to process sample 12 were put in 1 liter beakers respectively and were left for 10 days under the room temperature without being covered. After adding water equivalent to evaporated water to make 1 l respectively, sample 11 and sample 12 were processed again. Photographic properties for processing of sample 11 after leaving of alkali activator were hardly deteriorated but photographic properties were considerably deteriorated when sample 12 was processed after the developer was left. Especially the rise in the fog was remarkable.

As stated above, since the photographic light-sensitive material that contains the precursor of color developing agent of this invention is capable of being developed by alkali activator, the preservation efficiency of the processing solution improves remarkably.

[EXAMPLE 4]

A compound NB-17 (precursor of black and white developing agent) and a compound NB-20 (development inhibitor precursor) were dissolved in methanol and were added to silver iodo-bromide emulsion for the use of general black and white negative (including silver iodide of 5 mol%) and were coated on triacetate base so that the coating amount per 100 cm$^2$ is 40 mg for a compound NB-17 and 2.0 mg for a compound NB-20 and 25 mg for silver (sample 13).

After the sample 13 was given an ordinary wedge exposure, it was developed with 2% water solution of sodium carbonate 1 H$_2$O at 30° C. for two minutes and then, in an ordinary manner, was stopped, fixed and washed with water. The sample 13 thus processed had the low fog and was excellent in its sensitivity and maximum density.

Since the sample 13 contains both precursor of black and white developing agent of this invention and precursor of development inhibitor, it can be developed by alkali activator which contains only sodium carbonate and is very simple and it is possible to obtain an excellent photographic performance.

[EXAMPLE 5]

Silver iodo-bromide emulsion (including silver iodide of 5 mol%) for general black and white negative was coated so that the coating amount of silver per 100 cm$^2$ is 40 mg. On this layer, a compound NB-9, after being dissolved in methanol was mixed with gelatin water solution and was coated on the triacetate base. The coating amount of a compound NB-9 per 100 cm$^2$ was 3.3 mg (sample 14).

As a comparison, N,N,N', N'-tetramethyl-p-phenylenediamine (TMPD)2hydrochloride was dissolved in gelatin water solution instead of a compound 9 and was coated.

The coating volume of TMPD2hydrochloride per 100 cm$^2$ was 1.0 mg (sample 15).

Further, a sample not containing the compound NB-9 and TMPD2hydrochloride but being coated with only gelatin onto the said emulsion layer, was prepared. (sample 16).

After exposures are made onto the samples 14, 15 and 16 by making use of normal optical wedge, developments are made by the developing solution of which composition is as shown below at 30° C. for one minute, and then the initial development property is checked. After development was made, normal fixing and washing were made.

| Metol | 2.5 g |
|---|---|
| Hydroquinone | 2.5 g |
| Sodium sulphite anhydrous | 30 g |
| Sodium carbonate 1 H$_2$O | 10 g |
| Potassium bromide | 0.5 g |

| -continued |  |
|---|---|
| Add water to make | 1 l |

Furthermore, the above samples are stored for 24 hours under the conditions at 50° C. and at 80% of humidity and then a forced deterioration test was made.
The results obtained are shown in the table 3.

TABLE 3

| Sample Nos. | Compounds | Fog | Note * Specific sensitivity | Maximum density |
|---|---|---|---|---|
| Sample 14 (this invention) | NB - 9 | 0.05 | 145 | 2.2 |
| Sample 15 (other invention) | TMPD 2Hcl | 0.05 | 80 | 1.6 |
| Sample 16 (other invention) | nil | 0.05 | 100 | 1.6 |
| After forced deterioration | | | | |
| Sample 14 (this invention) | NB - 9 | 0.07 | 141 | 2.1 |
| Sample 15 (other invention) | TMPD 2Hcl | 0.05 | 63 | 0.8 |
| Sample 16 (other invention) | nil | 0.07 | 98 | 1.5 |

Note:
*The above specific sensitivity represents the relative sensitivity to that of the sample 16 (the one not having made a forced deterioration test) which is regarded as 100.)

It is found the facts from the table 3 that the sample 15 brings on a lot of desensitization and instability caused by time proceeding, but that the sample 14 is extremely superior in the initial development property and is reasonably better in stability with time proceeding, in comparison with those of the comparison samples 15 and 16.

Consequently, it can be obtained as the advantages that development of photographic sensitized material containing the compound NB-9 is greatly accelerated and the stability with time proceeding is not spoiled.

[EXAMPLE 6]

14 g of 4-amino-2,6-dichlorophenolhydrochloride are dissolved in 1 l of 10% gelatin solution, and then 24 g of sodium tetraphenyl borate, which are dissolved in 1 l of water with stirring at 40° C., are added therein. Further, the said gelatin solution is cooled by ice and set, after the said solution is stirred for several minutes. Then, the said set gelatin solution is cut in noodle form, washed by cool water, dissolved at 50° C., added water to make 3 l, added coating aid and hardening agent, and then coated onto a paper support which is resin-coated. On this layer, 2-[2-(2,4-di-t-pentylphenoxy)buthanamido]-4,6-dichloro-5-methylphenol, as a coupler, was coated after it was dissolved in dibutylphthalate and protect-dispersed in gelatin solution and then mixed with red-sensitive silver chlorobromide emulsion. The coating amount per 100 cm² of the above coupler was 3.0 mg and silver amount was 2.1 mg. Further on this layer, a protective layer was arranged by coating with 3% gelatin solution. (sample 17).

The sample 17 was exposed with white light by making use of step wedge and the following processing was made.

| Process | |
|---|---|
| Activator development at 35° C. | 3 min. |
| Bleaching and fixing at 35° C. | 1½ min. |
| Washing at 35° C. | 3 min. |
| Activator solution | |
| Sodium carbonate (1 H₂O) | 30 g |
| Potassium bromide | 1 g |

| -continued | |
|---|---|
| Add water to make | 1 l |

BLEACHING/FIXING SOLUTION

The same composed bleaching/fixing solution as the one used in the Example 1.

In the sample 17 that was processed by the above mentioned process, it was noted that the maximum density is high, no lowering of sensitivity is caused and almost nothing is stained. It was also confirmed that the superb photographic performance is displayed also in a forced deterioration test (under the same conditions as that in the Example 1).

What is claimed is:

1. A photographic material having a silver halide emulsion layer coated on a support, which material contains an ion compound which is composed from a compound having a quaternary nitrogen atom as a cation and a boron compound as an anion wherein the ion pair compound is represented by the following formula:

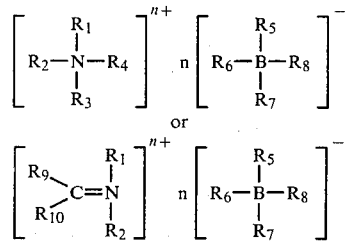

wherein $R_1$, $R_2$, $R_3$, $R_4$, $R_9$ and $R_{10}$ individually represent a hydrogen atom or hydroxyl, alkyl, alkenyl, cycloalkyl, aryl, phenyl, acyl, amino, carbamoyl, sulfonyl or heterocyclic groups, $R_1$ and $R_2$, or $R_1$, $R_2$, and $R_3$ may form a hetero nitrogen-containing ring by bonding to each other, $R_5$, $R_6$, $R_7$ and $R_8$ individually represent an alkyl, alkenyl, cycloalkyl, aryl, phenyl, heterocyclic or cyano group, an n is an integer from 1 to 5.

2. A photographic material according to claim 1 wherein the ion pair compound is represented by the following formula:

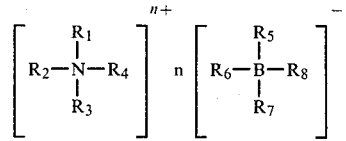

3. A photograhic material according to claim 2 wherein n represents an integer 1.

4. A photographic material according to claim 1 wherein the compound having a quaternary nitrogen atom is a derivative of a nitrogen containing organic base.

5. A photographic material according to claim 4 wherein the nitrogen containing organic base is a primary, secondary or tertiary amine compound.

6. A photographic material according to claim 5 wherein the organic base is a primary amine developing agent.

7. A photographic material according to claim 6 wherein the ion pair compound is incorporated in an adjacent layer of the silver halide emulsion layer.

8. A photographic material according to claim 1 wherein the silver halide emulsion layer contains a dye forming coupler.

* * * * *